United States Patent [19]

van Wijngaarden et al.

[11] Patent Number: 4,950,759

[45] Date of Patent: Aug. 21, 1990

[54] SUBSTITUTED 1,7-ANNELATED 1H-INDAZOLES

[75] Inventors: Ineke van Wijngaarden; Derk Hamminga; Hans H. Haeck; Wouter Wouters, all of Weesp, Netherlands

[73] Assignee: Duphar International Research B.V., Weesp, Netherlands

[21] Appl. No.: 374,736

[22] Filed: Jul. 3, 1989

[30] Foreign Application Priority Data

Jul. 7, 1988 [NL] Netherlands .................. 8801715

[51] Int. Cl.$^5$ .................. C07D 453/00; C07D 231/54; A61K 31/40; A61K 31/415
[52] U.S. Cl. ..................................... 546/94; 548/371
[58] Field of Search .................. 546/94; 544/252, 358; 514/253, 294

[56] References Cited

FOREIGN PATENT DOCUMENTS 297651 1/1989 European Pat. Off. .............. 546/94

*Primary Examiner*—Anton H. Sutto
*Assistant Examiner*—Celia Chang
*Attorney, Agent, or Firm*—Stevens, Davis, Miller & Mosher

[57] ABSTRACT

The invention relates to a group of new substituted 1,7-annelated 1H-indazole derivatives being strong and selective antagonists of "neuronal" 5-hydroxytryptamine (5-HT) receptors.

The compounds can be represented by general formula 1:

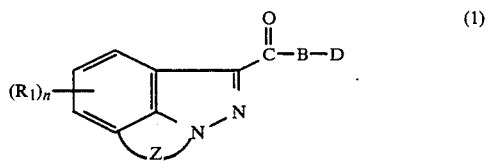

3 Claims, No Drawings

SUBSTITUTED 1,7-ANNELATED 1H-INDAZOLES

The invention relates to new 1,7-annelated 1H-indazole 3-carboxylic acid esters and amides of cyclic and polycyclic alcohols or amines, in which in the cyclic or polycyclic ring a carbon atom is replaced by a secondary nitrogen atom, or by a tertiary nitrogen atom or the N oxide hereof and to isometric compounds thereof, wherein the amide nitrogen atom is replaced by a carbon atom and to new imidazolylalkyl 1,7-annelated 1H-indazolyl-3-ketones and amides.

From European Patent Application No. 86302964.1 (publication No. 0.200.444) it is known inter alia that certain indazole carboxylic acid derivatives are 5 HT-antagonists which may be used for the treatment of serotonin-induced syndromes.

It has been found surprisingly that the new compounds of formula 1

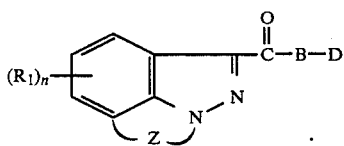

wherein
- R₁ is straight or branched alkyl having 1-4 C-atoms; fluorinated alkyl having 1 or 2 C-atoms or two alkyl groups R₁ bonded to adjacent carbon atoms together form a carboxylic ring, or R₁ is straight or branched alkoxy or alkylthio having 1-4 C-atoms which may be substituted with one or more fluorine atoms, or two alkoxy- and/or alkylthio groups R₁ bonded to adjacent carbon atoms may form a ring consisting of 5-7 ring atoms or R₁ is a cycloalkoxy group or cycloalkylthio group having 3-6 C-atoms, or R₁ is straight or branched (C₁₋₄)alkoxy- or (C₁₋₄)alkylthio-(C₁₋₂)alkyl, or R₁ is an alkoxycarbonylmethyl group having 1-4 C-atoms in the alkoxy group, or R₁ is a group R₂R₃N-SO₂-CH₂-, R₂R₃N-CO-CH₂-, R₂R₃N-CO- or R₂R₃N-SO₂- wherein R₂ and R₃ independently of each other are hydrogen alkyl having 1-3 C-atoms, or together with the nitrogen atom form a heterocyclic 5- or 6-ring, or R₁ is hydroxy, halogen, cyano, straight or branched alkoxycarbonyl having 1-4 C-atoms in the alkyl group;
- n has the value 0-2;
- Z together with the carbon atom and the nitrogen atom and the intermediate carbon atom forms a heterocyclic group consisting of 5-8 ring atoms in which, in addition to the nitrogen atom already present, a second hetero atom from the group O, S, or SO₂ may be present, which ring may be substituted with alkyl groups or with a spiroalkyl group (C₂₋₅), or which ring may be annelated with a saturated or non-saturated carbocyclic or heterocyclic ring which consists of 5- or 6-ring atoms and which may be substituted with halogen, alkyl or alkoxy having 1-2 C-atoms;
- B represents an oxygen atom or a group —CH(R₄)— or —NR₄—, wherein R₄ is hydrogen straight or branched alkyl having 1-6 C-atoms, or benzyl;
- D is a group (CH₂)ₘ-R₅, wherein m has the value 0, or 1 and R₅ is an optionally substituted imidazole group, or a carbocyclic or polycarbocyclic ring system in which one carbon atom is replaced by a secondary nitrogen atom, or by a tertiary nitrogen atom or the N-oxide hereof, and the pharmacologically acceptable acid addition salts thereof are very strong and selective antagonists of "neuronal" 5-hydroxytryptamine (5-HT) receptors.

The group D is preferably a group of the formula 2 to 9

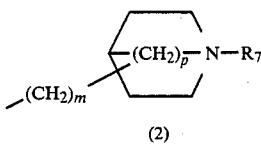

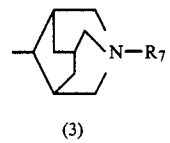

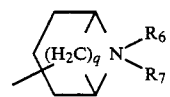

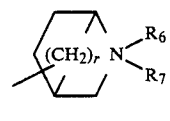

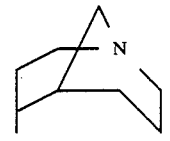

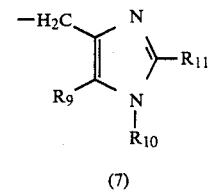

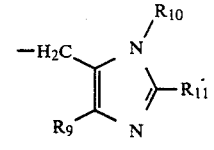

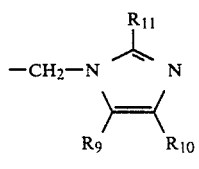

wherein p has the value 1 or 2, m has the value 0 or 1, q is 2, 3 or 4, r is 1, 2 or 3, and wherein $R_6$ is hydrogen, $(C_{1-6})$alkyl, $(C_{3-6})$cycloalkyl, $(C_{3-6})$cycloalkyl-$(C_{1-2})$alkyl, allyl or $(C_{3-5})$-alkynyl, or wherein $R_6$ is a group $(CH_2)_r$-$R_8$, wherein t is 1 or 2 and $R_8$ is phenyl, thienyl, pyrrolyl, or furyl, which groups may be substituted with 1 or 2 substituents of the group hydroxy, $(C_{1-4})$alkyl, $(C_{1-4})$alkoxy, trifluoromethyl, halogen and nitrile and wherein $R_7$ is absent or is an oxygen atom, and wherein one of the groups $R_9$, $R_{10}$ and $R_{11}$ is hydrogen, alkyl having 1-4 C-atoms, cycloalkyl having 3-6 C-atoms or alkenyl having 2-4 C-atoms, and the two other groups are independently of each other hydrogen or alkyl having 1-4 C-atoms.

Examples of suitable acids with which the compounds of formula 1 according to the invention can form pharmaceutically acceptable acid addition salts are hydrochloric acid sulphuric acid, phosphoric acid, nitric acid, and organic acids, for example, citric acid, fumaric acid, maleic acid, tartaric acid, acetic acid, benzoic acid, p-toluene sulphonic acid, methane sulphonic acid, and the like.

The invention includes both the racemates and (geometric) isomers and the individual enantiomers of compounds of formula 1.

The antagonistic activity of the compounds of formula 1 on the response induced by 5-HT or 2-methyl-5HT was determined and measured in the Bezold Jarish reflex test in rats. The affinity to "neuronal" 5HT receptors was determined and measured by the displacement of (3H)GR 38032F of neuroblastoma cells.

On the basis of the antagonistic activity on this type of 5-HT receptors, the compounds may be used for the treatment of symptoms which are caused by overexcitation of the said receptors (a) in the gastrointestinal system (nausea and vomiting as a result of exogenic factors, for example cancer therapy, or endogenic factors, for example stasis of the stomach and migraine) ulcer, dyspepsia, spasms, irritable bowel syndrome, etc. or (b) in the central nervous system (hallucinations, delusions, manias, depressions, fear, pain, nausea, improvement of vigilance, etc.), or (c) in the cardiovascular system, for example, spasms of the vessels, arrhytmia, etc., or (d) in the respiratory system (including nasal disturbances and disturbances of bronchi and lungs, or (e) to alleviate or prevent withdrawal-effects induced by abuse of drugs.

The compounds according to the invention and their salts may be brought into forms suitable for administration, for example, pills, tablets, coated tablets, capsules, powder, injection liquids, and the like by means of techniques conventionally used for this purpose and while using suitable auxiliary substances, for example, solid or liquid carrier materials.

The dosage in which the compounds according to the invention may be used depends on the severity and the nature of the disease to be treated and the way of administration. As a rule, the daily dosage will be between 0.05 and 20 mg, preferably between 0.1 and 10 mg of active substance.

The compounds according to the invention may be prepared in a manner known for analogous compounds, for example: (a) by reaction of a compound of formula 10

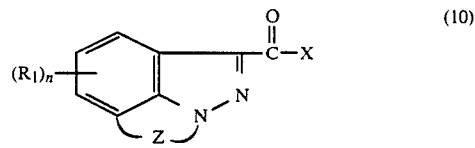

wherein $R_1$, n and Z have the above-mentioned meanings, and X is a group which may be replaced by a nucleophile, for example, a halogen atom, a group of formula 11

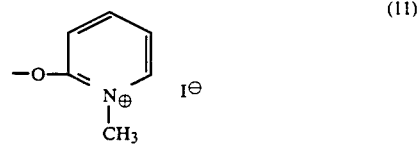

a group —O—CO—O—alkyl etc., with a compound of the formula Y—B—D wherein Y is a hydrogen atom or an alkali metal atom, B is oxygen or a group —N($R_4$)—, wherein $R_4$ has the meaning given above, and D has the meaning given in formula 1, or is a group $D^1$ which gives a group D after removal of a protective group. The reaction is preferably carried out in a suitable solvent, for example, dichloromethane, pyridine, methanol, acetonitrile, dimethylformamide, toluene, etc.

In particular, compounds of formula 12

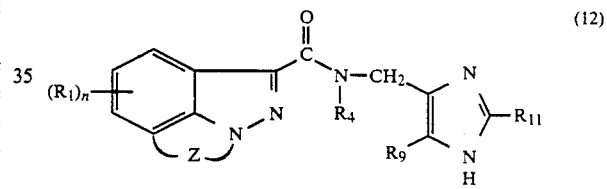

wherein $R_1$, $R_4$, $R_9$, $R_{11}$, n and Z have the meanings given in formula 1, can be obtained in good yield by reacting a compound of formula 10 with a compound of formula 13 or 14

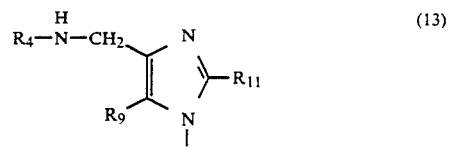

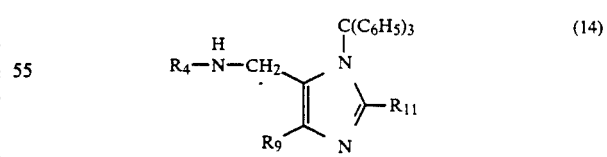

and then removing the trityl group from the product obtained, for example in acid conditions or with palladium on carbon and ammonium formate, preferably in a suitable solvent.

(b) by substitution of the amine hydrogen atom in group D in a compound of formula 1, wherein $R_1$, n, Z, B, and D have the meanings mentioned in formula 1 with the proviso that the ring nitrogen atom in group D is a secondary nitrogen atom, by a group $R_6$, wherein $R_6$ has the meaning given in formula 1, for example, by reaction of a compound of formula 1 with a suitable aldehyde or ketone under reducing conditions, or with a suitable halogen compound. The reaction is preferably carried out in a suitable solvent, for example, water, ethanol, dimethylformamide, etc., at temperatures between 0° and 150° C.; or (c) by reaction of a compound of formula 15 or 16

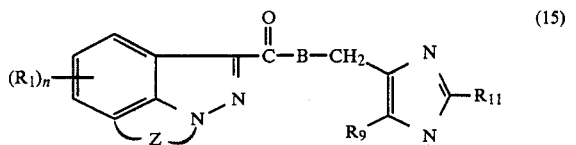
(15)

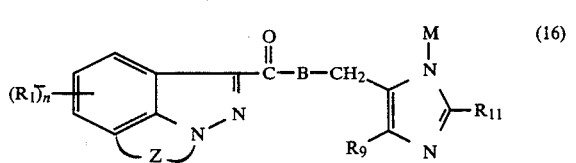
(16)

wherein $R_1$, n, Z, $R_9$, and $R_{11}$ have the meanings given in formula 1, M is an alkalimetal atom, and B is a group $-N(R_4)-$ or $-CH(R_4)-$, with a compound of the formula $R_{10}-X$, wherein $R_{10}$ has the above-mentioned meaning and X is a group or atom which can be replaced by a nucleophile like a halogen atom. The reaction is preferably carried out in a suitable solvent, for example ethanol, dimethylformamide, etc., or (d) by reaction of a compound of formula 17

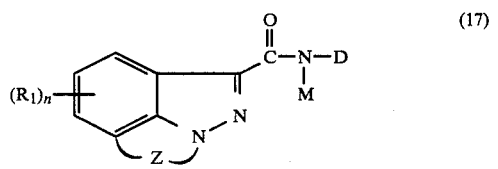
(17)

wherein $R_1$, n, Z, and D have the meanings given in formula 1 on the understanding that $R_6$ in formulae 4 and 5, and $R_{10}$ in formulae 7 and 8 do not have the meaning hydrogen and that $R_7$ is absent, and wherein M is an alkalimetal atom, with a compound of the formula $R_4-X$, wherein X is halogen. The reaction is preferably carried out in a organic solvent, for example tetrahydrofuran or hexane; or (e) by reaction of a compound of formula 18

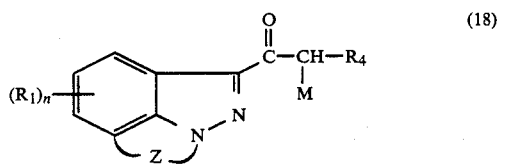
(18)

wherein $R_1$, $R_4$, n and Z have the meaning given in formula 1, and (1) when M is a hydrogen atom, with a compound of formula 19 or 20

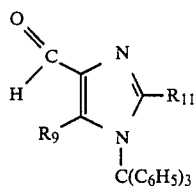
(19)

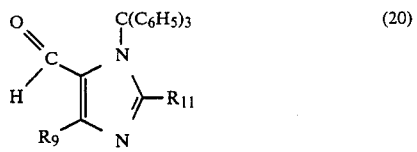
(20)

wherein $R_9$ and $R_{11}$ have the meanings given in formula 1, preferably in a suitable solvent in alkaline conditions, hydrogenating the obtained product for example with palladium as a catalyst in a suitable solvent and removing the trityl group in acid conditions, or (2) when M is an alkaline atom with a compound of formula 21 or 22

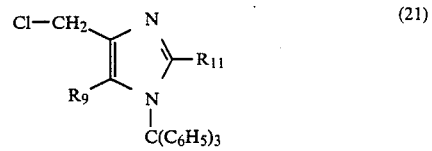
(21)

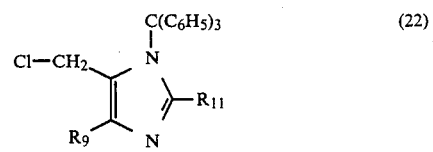
(22)

and removing the trityl group from the obtained product in acid conditions or with palladium and ammonium formate, giving compounds of formula 1 wherein B is a group of the formula $-CH(R_4)-$ and D is group of formula 7 or 8 wherein $R_{10}$ is hydrogen; or (f) by reaction of a compound of formula 23

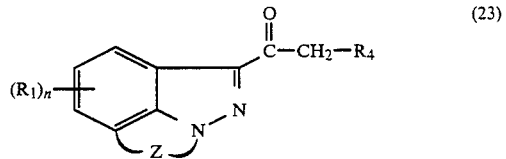
(23)

wherein $R_1$, $R_4$, n and Z have the meaning given in formula 1, with dimethylamine hydrochloride and formalin, preferably in a suitable solvent, for example glacial acetic acid or ethanolic hydrochloric acid, at temperatures between 20° and 150° C., followed by reaction of the so-obtained Mannich-base with a compound of formula 24

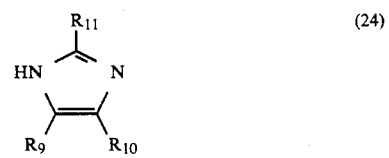
(24)

wherein $R_9$, $R_{10}$ and $R_{11}$ have the meaning given in formula 9, preferably in a suitable solvent, for example water, diluted ethanol, dimethylformamide, etc., giving high yields of compounds of formula 1 wherein D is a group of formula 9; or (g) by transesterification of a compound of formula 25

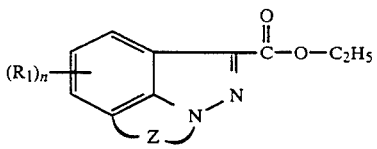

wherein $R_1$, n and Z have the meaning given in formula 1, with a cyclic or polycyclic alcohol wherein a carbon atom is replaced by a nitrogen atom, for example tropine, N-methylgranatoline, etc., preferably under the influence of active sodium methanolate in a suitable solvent, for example toluene, xylene, etc, at temperatures between 20° and 180° C.

The invention will now be described in greater detail with reference to the ensuing specific examples.

EXAMPLE I

N-(endo-8-methyl-8-azabicyclo[3,2,1]oct-3-yl)-7,8-dihydro-6H-pyrazolo[4,5,1-ij]quinoline-2-carboxamide 0.75 g (3.7 mmol) of 7,8-dihydro-6H-pyrazolo[4,5,1-ij]quinoline-2-carboxylic acid and 0.52 g (3.7 mmol) of endo-3-amino-8-methyl-8-azabicyclo[3,2,1]octane and 1.14 g (4.5 mmol) of 2-chloro-1-methyl-pyridinium iodide and 0.9 g (9 mmol) of triethylamine were brought into 30 ml of methylene chloride and the mixture was boiled for 1 hour while stirring. The mixture was then cooled and shaken two times with a 5% solution of sodium bicarbonate in water. The methylene chloride layer was evaporated in vacuum and the residue was chromatographed over silica gel using methylene chloride/methanol/ammonia in the ratio 84/15/1 as an eluent.

The desired fraction was evaporated in vacuum. The residue was dissolved in ethyl acetate. 1.1 Equivalent of alcoholic hydrochloric acid were added, the solid was sucked off, washed with ethyl acetate and dried. Yield: 1.1 g (82%); melting-point: 285° C. (decomposition)

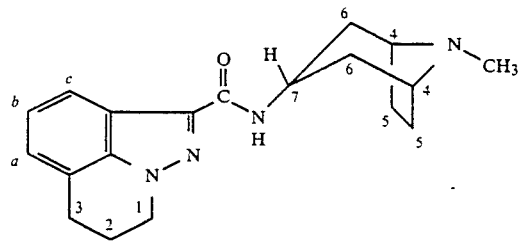

1H NMR (400 MHz, CDCl3; ref. TMS)

| | |
|---|---|
| 8.05 (Hc, J = 8 Hz) | 3.03 (2 × H3, J = 6 Hz) |
| 7.46 (NH, J ≈ 7 Hz) | 2.35 (2 × H2, J = 6 Hz) |
| 7.18 (Hb, J ≈ 7 Hz and 8 Hz) | 2.32 (N—CH3) |
| 7.09 (Ha, J ≈ 7 Hz) | 2.30 (2 × H6, multiplet) |
| 4.41 (2 × H1, J = 6 Hz) | 2.25–1.90 (multiplet, 4H) |
| 4.33 (H7, multiplet) | 1.83 (2 × H6, multiplet) |
| 3.19 (2 × H4, multiplet) | |

In an analogous manner N-(endo-9-methyl-9-azabicyclo[3,3,1]-non-3-yl)-7,8-dihydro-6H-pyrazolo[4,5,1-ij]quinoline-2-carboxamide was obtained as an amorphous substance. Yield: 60% 1H NMR (400 MHz, CDCl3; ref TMS)

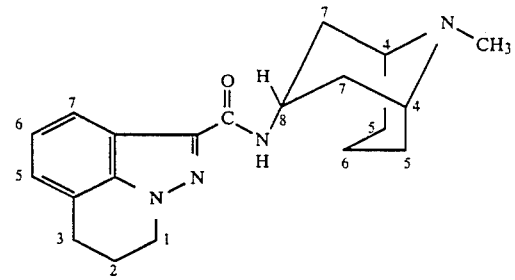

| | |
|---|---|
| 8.07 (Hc; J=1 Hz and 8 Hz) | 2.6–2.5 (2×H7 eq. multiplet) |
| 7.17 (Hb; J=7 Hz and 8 Hz) | 2.53 (N–CH3) |
| 7.09 (Ha; J=1 Hz and 7 Hz) | 2.36 (2×H2, J=6 Hz) |
| 6.79 (NH, J=8 Hz) | 2.10–1.9 (multiplet, 3H) |
| 4.65 (H8, J=7, 8 and 11 Hz) | 1.60–1.48 (multiplet, 1H) |
| 4.39 (2×H1, J=6 Hz) | 1.40 (2×H7 ax, J=3, 11 and 14 Hz) |
| 3.11 (2×H4, multiplet) | |
| 3.02 (2×H3, J=6 Hz) | 1.14–1.02 (multiplet, 2H) |

EXAMPLE II

N-(1-azabicyclo[2,2,2]oct-3-yl)-7,8-dihydro-6H-pyrazolo[4,5,1-ij]quinoline-2-carboxamide-hydrochloride 0.3 g (1.5 mmol) of 7,8-dihydro-6H-pyrazolo[4,5,1-ij]quinoline-2-carboxylic acid were dissolved in 10 ml of methylene chloride. 1 ml of thionyl chloride was added and the mixture was boiled for 1 hour. The mixture was then evaporated in vacuum. 10 ml of methylene chloride, 1.0 g (7.9 mmol) of 3-aminoquinuclidine and 1.0 g (10 mmol) of triethylamine were added after which the mixture was stirred for 30 minutes. The mixture was then extracted with water. The methylene chloride layer was separated, washed with water, dried and evaporated in vacuum. The residue was chromatographed over silica gel using methylene chloride/methanol/ammonia in the ratio 84:15:1 as an eluent; Yield; 0.15 g (33%); melting point 146°–147.5° C. 13C NMR (CDCl3, ref.: TMS)

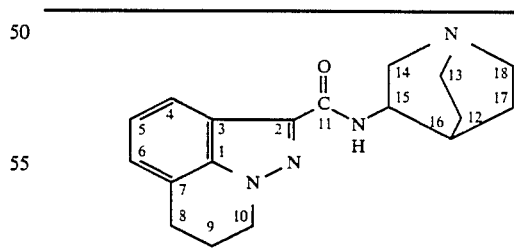

| | | |
|---|---|---|
| 1 | 139.26 | S |
| 2 | 136.81 | S |
| 3 | 122.01 | S |
| 4 | 119.68 | D |
| 5 | 122.80 | D |
| 6 | 123.46 | D |
| 7 | 120.44 | S |
| 8 | 23.85 | T |
| 9 | 23.02 | T |
| 10 | 46.76 | T |
| 11 | 162.83 | S |

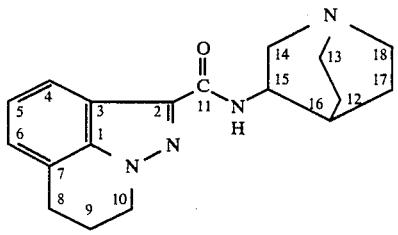

| 12 | 25.28 | T |
| 13 | 47.33 | T |
| 14 | 55.56 | T |
| 15 | 45.96 | D |
| 16 | 25.83 | D |
| 17 | 19.88 | T |
| 18 | 46.59 | T |

EXAMPLE III

N-(1-azabicyclo[2,2,2]oct-3-yl)-6,7,8,9-tetrahydropyrazolo[4,5,1-jk][1]benzazepine-2-carboxamide hydrochloride 0.75 g (3.5 mmol) of 6,7,8,9-tetrahydropyrazolo[4,5,1-jk][1]benzazepine-2-carboxylic acid were boiled for 3 hours in 12 ml of thionyl chloride. Access of thionyl chloride was then removed by distillation under reduced pressure. 10 ml of toluene were added, and distillation under reduced pressure was repeated. The residue was dissolved in 10 ml of acetonitrile, and 0.83 g (6.6 mmol) of 3-amino-quinuclidine were added. The mixture was stirred for 18 hours at 20° C., then shaken with 2N sodium hydroxide and with methylene chloride. The methylene chloride layer was washed with water, dried and evaporated. The residue was dissolved in a mixture of 5 ml of absolute alcohol and 5 ml of ethyl acetate. The reaction mixture of 0.65 ml of acetyl chloride with 2 ml of absolute alcohol was added to the obtained solution and kept at 0° C. for 18 hours. The solid was then sucked off, washed with ethyl acetate and dried. In this manner 1.12 g of the desired product was obtained. The product decomposed slowly at 280° C. $^{13}$C NMR (CDCl$_3$, ref: TMS)

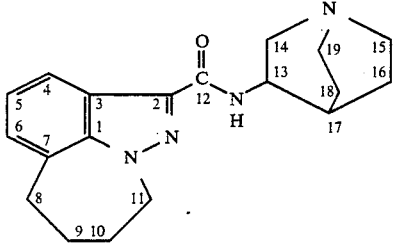

| 1 | 141.83 | S |
| 2 | 137.46 | S |
| 3 | 125.35 | S |
| 4 | 120.20 | D |
| 5 | 126.78 | D |
| 6 | 122.62 | D |
| 7 | 124.26 | S |
| 8 | 28.10 | T |
| 9 | 27.21 | T |
| 10 | 35.03 | T |
| 11 | 54.75 | T |
| 12 | 162.66 | S |
| 13 | 46.27 | D |

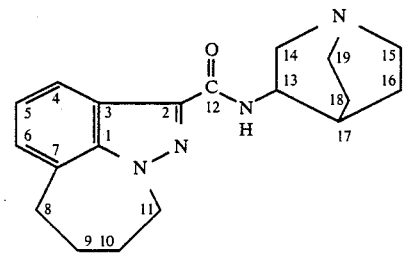

| 14 | 56.22 | T |
| 15 | 47.57 | T |
| 16 | 25.91 | T |
| 17 | 26.00 | D |
| 18 | 20.34 | T |
| 19 | 46.79 | T |

In a similar manner was obtained:

N-(endo-8-methyl-8-azabicylo[3,2,1]oct-3-yl)-6,7,8,9-tetrahydro-pyrazolo[4,5,1-jk][1]benzazepine-2-carboxamide hydrochloride; melting point: starting at 290° C. (decomposition) $^{13}$C NMR(CDCl$_3$, Ref.:TMS, additive: triethylamine)

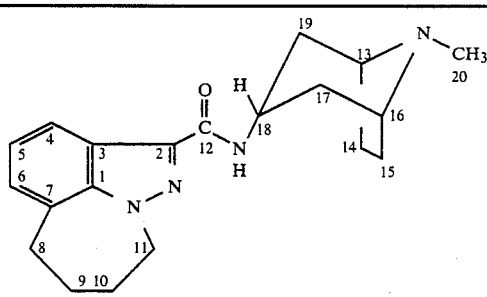

| 1 | 141.83 | S |
| 2 | 137.56 | S |
| 3 | 125.38 | S |
| 4 | 120.03 | D |
| 5 | 126.70 | D |
| 6 | 122.52 | D |
| 7 | 124.10 | S |
| 8 | 28.03 | T |
| 9 | 27.17 | T |
| 10 | 34.96 | T |
| 11 | 54.74 | T |
| 12 | 161.90 | S |
| 13 | 60.42 | D |
| 14 | 25.55 | T |
| 15 | 25.55 | T |
| 16 | 60.42 | D |
| 17 | 36.00 | T |
| 18 | 40.52 | D |
| 19 | 36.00 | T |
| 20 | 39.91 | Q |

EXAMPLE IV 7,8-dihydro-6H-pyrazolo[4,5,1-ij]quinoline-2-carboxylic acid (endo-8-methyl-8-azabicyclo[3,2,1]oct-3-yl)ester 0.7 g (30 mmol) of sodium were reacted with 15 ml of methanol. 50 ml of toluene were added then, and the solvent was removed by distillation until a boiling point of 110° C. was reached. 2.9 g (12 mmol) of 7,8-dihydro-6H-pyrazolo[4,5,1-ij]quinoline-2-carboxylic acid ethyl ester (obtained by reaction of the corresponding acid chloride with ethanol and triethylamine), and a solution of 3.5 g (25 mmol) of inaqueous tropine in 25 ml of toluene were added to the suspension obtained. The mixture was boiled for 1 hour while slowly distilling off the solvent. The mixture was cooled, methylene chloride was added, and washing with saline was carried out. The product was dried and evaporated under reduced pressure. The residue was chromatographed over silica gel using methanol/triethylamine (97/3) as an eluent. 2.2 g of the desired product were obtained having a melting point of 126°–128° C. $^{13}$C NMR (CDCl$_3$, Ref.: TMS).

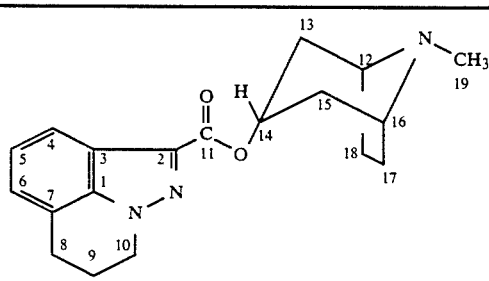

| 1 | 139.05 | S |
| 2 | 134.89 | S |
| 3 | 122.48 | S |
| 4 | 118.98 | D |
| 5 | 122.72 | D |
| 6 | 123.80 | D |
| 7 | 121.13 | S |
| 8 | 23.94 | T |
| 9 | 23.02 | T |
| 10 | 47.21 | T |
| 11 | 162.60 | S |
| 12 | 59.76 | D |
| 13 | 36.68 | T |
| 14 | 68.23 | D |
| 15 | 36.68 | T |
| 16 | 59.76 | D |
| 17 | 25.86 | T |
| 18 | 25.86 | T |
| 19 | 40.41 | Q |

In a similar manner was obtained 6,7,8 9-tetrahydropyrazolo[4,5 1-jk][1]benzazepine-2-carboxylic acid (endo-8-methyl-8-azabicyclo[3,2,1]oct-3-yl)ester hydrochloride. Melting-point: 280° C. (slow decomposition) $^{13}$C NMR (CDCl$_3$, Ref. TMS, additive:triethylamine)

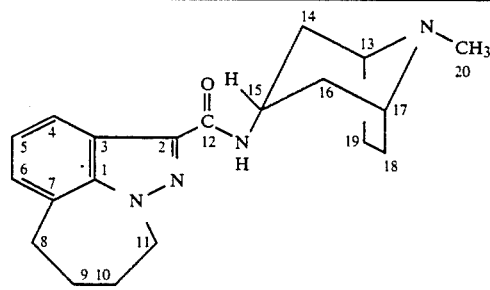

| 1 | 141.44 | S |
| 2 | 135.33 | S |
| 3 | 124.79 | S |
| 4 | 119.21 | D |
| 5 | 122.96 | D |
| 6 | 126.61 | D |
| 7 | 125.89 | S |
| 8 | 27.85 | T |

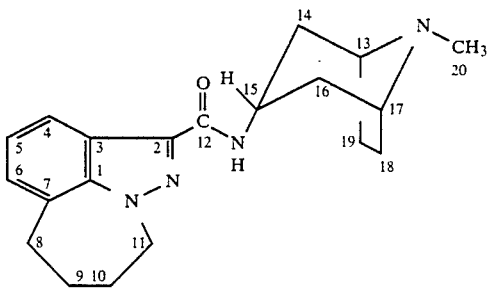

| 9 | 27.08 | T |
| 10 | 34.66 | T |
| 11 | 54.99 | T |
| 12 | 162.39 | S |
| 13 | 60.09 | D |
| 14 | 36.35 | T |
| 15 | 67.90 | D |
| 16 | 36.35 | T |
| 17 | 60.09 | D |
| 18 | 25.70 | T |
| 19 | 25.70 | T |
| 20 | 40.22 | Q |

EXAMPLE V

N-methyl-N-{(4-methyl-imidazol-5-yl)methyl}-7,8-dihydro-6H-pyrazolo[4,5,1-ij]quinoline-2-carboxamide hydrochloride 1,9 g (4.95 mmol) of 7,8-dihydro-6H-pyrazolo[4,5,1-ij]quinoline- 2-carboxylic acid was added to 15 ml of thionyl chloride, and boiled for 2.5 hours. Thionyl chloride was distilled off under reduced pressure, 10 ml of toluene were added and distilling off was repeated. The residue was dissolved in 20 ml of acetonitrile, and a solution of 1.84 g (5 mmol) of the mixture of isomers of N-methyl-N{(4-methyl-1-triphenylmethyl-1H-imidazol-5-yl)methyl}amine and N-methyl-N-{(5-methyl-1-triphenylmethyl-1H-imidazol-4-yl)methyl}amine and 1.4 ml (10 mmol) of triethylamine in 20 ml of acetonitrile were added. The mixture was boiled for 1 hour and evaporated in vacuum. The residue was shaken with 2N sodium hydroxide and with methylene chloride. The methylene chloride layer was separated, washed with brine and evaporated in vacuum. The so obtained crude N-methyl-N-{(4(or 5)-methyl-1-triphenylmethyl-1H-imidazol-5(or 4)-yl)methyl}-7,8-dihydro-6H-pyrazolo[4,5,1-ij]quinoline-2-carboxamide was boiled for 1 hour in a mixture of 50 ml of acetic acid and 50 ml of water, and cooled to 10° C. The solid was sucked off and washed with water. The filtrate was made neutral with soda and extracted with methylene chloride successively. The organic layer was evaporated in vacuum, and the residue was purified by column chromatography over silicagel, using methylene chloride/methanol (95/5) as an eluent. After evaporating the desired fractions the free base of the desired product was obtained, and dissolved in a mixture of 4 ml of isopropanol and 2 ml of ethyl acetate. After the addition of alcoholic hydrochloric acid (i.e. the reaction mixture of 0.5 ml of acetyl chloride and 1.5 ml of absolute alcohol) a precipitate was formed. The precipitate was sucked off after 2 hours, washed with ethyl acetate and dried 1 g (58%) of the desired hydrochloride was obtained having a melting point of 208°–209° C. 13C NMR (CDCl3, Ref,: TMS, additive: triethylamine):

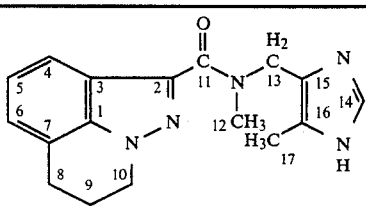

MIXTURE OF 2 AMIDE ISOMERS: MOST LINES ARE BROADENED

| 1 | 138.56 | S |
| 2 | 137.78 | S |
| 3 | 122.07 | S |
| 4 | 119.56 | D |
| 5 | 122.70 | D |
| 6 | 123.21 | D |
| 7 | 121.98 | S |
| 8 | 23.97 | T |
| 9 | 23.07 | T |
| 10 | 46.83 | T |
| 11 | 164.72 | S |
| 12 | 32.94 | Q |
| 13 | 43.08 | T |
| 14 | 134.02 | D |
| 15 | 131.60 | S |
| 16 | 124.98 | S |
| 17 | 11.00 | Q |
| 1 | 138.37 | S |
| 2 | 137.79 | S |
| 3 | 122.07 | S |
| 4 | 119.78 | D |
| 5 | 123.15 | D |
| 6 | 123.01 | D |
| 7 | 121.98 | S |
| 8 | 23.97 | T |
| 9 | 23.07 | T |
| 10 | 46.83 | T |
| 11 | 163.83 | S |
| 12 | 36.80 | Q |
| 13 | 45.29 | T |
| 14 | 133.60 | D |
| 15 | 129.93 | S |
| 16 | 126.90 | S |
| 17 | 11.23 | Q |

In a similar manner were obtained:

(1) N-55 (4-methyl-imidazol-5-yl)methyl}-7,8-dihydro-6H-pyrazolo[4,5,1-ij]quinoline-2-carboxamide hydrochloride. Yield: 52%, melting point: 257°–259° C. (decomposition) 13C NMR (CDCl3, Ref.: TMS, additive: triethylamine

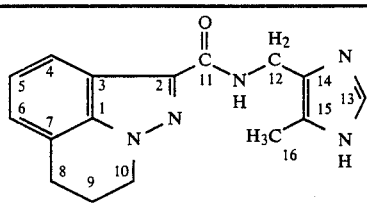

| 1 | 139.22 | S |
| 2 | 136.78 | S |
| 3 | 122.06 | S |
| 4 | 119.57 | D |
| 5 | 122.68 | D |
| 6 | 123.35 | D |
| 7 | 120.43 | S |
| 8 | 23.89 | T |
| 9 | 23.00 | T |
| 10 | 46.73 | T |
| 11 | 163.05 | S |

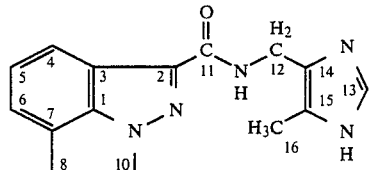

| 12 | 34.72 | T |
| 13 | 133.60 | D |
| 14 | 129.31 | S |
| 15 | 126.81 | S |
| 16 | 10.35 | Q |

(2) N-methyl-N-{(4-methyl-imidazol-5-yl)methyl}-6,7,8,9-tetrahydro-pyrazolo [4,5,1-jk][1]benzazepine-2-carboxamide hydrochloride.

Yield: 75%; melting point: 208°–209° C. 13C NMR (CDCl3, Ref.: TMS, additive: triethylamine)

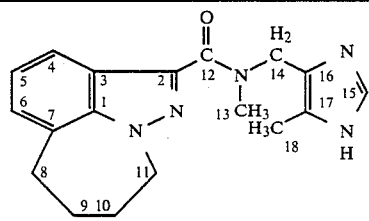

MIXTURE OF 2 AMIDE ISOMERS: MOST LINES ARE BROADENED

| 1 | 141.15 | S |
| 2 | 138.77 | S |
| 3 | 125.49 | S |
| 4 | 119.78 | D |
| 5 | 127.23 | D |
| 6 | 122.33 | D |
| 7 | 125.34 | S |
| 8 | 28.10 | T |
| 9 | 27.16 | T |
| 10 | 35.15 | T |
| 11 | 54.79 | T |
| 12 | 163.63 | S |
| 13 | 32.78 | Q |
| 14 | 42.89 | T |
| 15 | 134.01 | D |
| 16 | 129.77 | S |
| 17 | 126.95 | S |
| 18 | 11.26 | Q |
| 1 | 140.87 | S |
| 2 | 138.63 | S |
| 3 | 125.49 | S |
| 4 | 119.45 | D |
| 5 | 126.68 | D |
| 6 | 122.05 | D |
| 7 | 125.34 | S |
| 8 | 28.10 | T |
| 9 | 27.16 | T |
| 10 | 35.11 | T |
| 11 | 54.65 | T |
| 12 | 164.58 | S |
| 13 | 36.77 | Q |
| 14 | 45.27 | T |
| 15 | 133.60 | D |
| 16 | 131.85 | S |
| 17 | 124.57 | S |
| 18 | 10.93 | Q |

(3) N-{(4-methyl-imidazol-5-yl)methyl}-6,7,8,9-tetrahydropyrazolo[4,5,1-[1]benzazepine-2-carboxamide hydrochloride.

Yield: 94%; melting point: 261°–262° C. (decomposition) $^{13}$C NMR (CDCl$_3$, Ref.: TMS, additive: Triethylamine)

| | | |
|---|---|---|
| 1 | 141.57 | S |
| 2 | 137.01 | S |
| 3 | 125.43 | S |
| 4 | 119.72 | D |
| 5 | 126.64 | D |
| 6 | 122.51 | D |
| 7 | 124.09 | S |
| 8 | 27.93 | T |
| 9 | 27.09 | T |
| 10 | 34.95 | T |
| 11 | 54.68 | T |
| 12 | 162.82 | S |
| 13 | 33.91 | T |
| 14 | 132.88 | D |
| 15 | 126.55 | S |
| 16 | 128.89 | S |
| 17 | 9.93 | Q |

EXAMPLE VI 1-(7,8-dihydro-6H-pyrazolo[4,5,1-ij]quinoline-2-yl)-3-(2-methyl-1H-imidazol-1-yl)-propan-1-one 1.5 g (7.5 mmol) of 2-acetyl-7,8-dihydro-6H-pyrazolo[4,5,1-ij]quinoline together with 0.45 g (15 mmol) of paraformaldehyde and 1.35 g (16 mmol) of dimethylammonium chloride in 50 ml of acetic acid was stirred for 2 hours at 100° C. The mixture was evaporated in vacuum, and the residue was shaken with a mixture of methylene chloride and sodium hydroxide solution. The organic layer was washed with saline and evaporated in vacuum. The residue was chromatographed over silicagel using methylene chloride/methanol/ammonia (92.5/7/0.5) as an eluent. The desired fractions were evaporated in vacuum, and the residue was dissolved in alcoholic hydrochloric acid. 0.76 g (35%) of 1-(7,8-dihydro-6H-pyrazolo[4,5,1-ij]quinoline-2-yl)-3-(N,N-dimethylamino)-propan-1-one hydrochloride were obtained after evaporating in vacuum. This product (0.76 g, 2.6 mmol) was boiled for 18 hours together with 1 g (12 mmol) of 2-methyl-imidazole in a mixture of 20 ml of water and 5 ml of propanol-1. The mixture was diluted with 2N sodium hydroxide and extracted with methylene chloride. The organic layer was separated and evaporated in vacuum. The residue was chromatographed over silicagel using methylene chloride/methanol/ammonia (92.5/7/0.5) as an eluent. 0.5 g (69%) of the desired product were obtained; melting point 133°–134° C. $^{13}$C NMR (CDCl$_3$, Ref.: TMS):

| | | |
|---|---|---|
| 1 | 139.23 | S |
| 2 | 141.49 | S |
| 3 | 122.32 | S |
| 4 | 119.78 | D |
| 5 | 123.27 | D |
| 6 | 124.79 | D |
| 7 | 120.56 | S |
| 8 | 23.86 | T |
| 9 | 23.08 | T |
| 10 | 47.25 | T |
| 11 | 192.98 | S |
| 12 | 39.50 | T # |
| 13 | 40.95 | T # |
| 14 | 144.53 | S |
| 15 | 127.13 | D |
| 16 | 119.26 | D |
| 17 | 13.05 | Q |

EXAMPLE VII 1-(7,8-dihydro-6H-pyrazolo[4,5,1-ij]quinolin-2-yl)-3-(4-methyl-imidazol-5-yl)-propan-1-one (a)

1-(7,8-dihydro-6H-pyrazolo[4,5,1-ij]quinolin-2-yl)-3-(5-methyl-1-triphenylmethyl-1H-imidazol-4-yl)-2-propoen-1-one 1 g (5 mmol) of 2-acetyl-7,8-dihydro-6H-pyrazolo[4,5,1-ij]quinoline and 1.76 g (5 mmol) of 4-formyl-5-methyl-1-triphenylmethyl-1H-imidazole were dissolved in 70 ml of ethanol. 5 ml of 2N sodium hydroxide were added, and the mixture was boiled for 48 hours. Ammonium acetate was then added, the solvent was evaporated in vacuum, and the residue was shaken with water and with methylene chloride. The organic layer was separated, washed with water, and evaporated in vacuum. The residue was chromatographed on silicagel using methylene chloride/ethyl acetate (3/1) as an eluent. After evaporating the desired fractions 2.3 g (86%) of the product was obtained.

(b)

1-(7,8-dihydro-6H-pyrazolo[4,5,1-ij]quinolin-2-yl)-3-(5-methyl-1-triphenylmethyl-1H-imidazol-4-yl)-propan-1-one 2.2 g of the product obtained according to a) was hydrogenated for 12 hours at 20° C. on 0.86 g of 10% palladium on carbon in a mixture of 50 ml of methanol and 50 ml of ethyl acetate. The catalyst was removed by filtration, and the filtrate was evaporated in vacuum. The residue was chromatographed over silicagel using methylene chloride/methanol (98/2) as an eluent. After evaporating the desired fractions 1.2 g (54.3%) of the desired product were obtained.

(c)

1-(7,8-dihydro-6H-pyrazolo[4,5,1-ij]quinolin-2-yl)-3-(4-methyl-imidazol-5-yl)-propan-1-one 1,2 g (2.24 mmol) of the product obtained in (b) was boiled for 1 hour in a mixture of 30 ml of acetic acid and 30 ml of water. The mixture was cooled and filtrated. The filtrate was evaporated in vacuum, and the residue was shaken with a mixture of 2N sodium hydroxide and methylene chloride. The organic layer was washed with water, dried and evaporated in vacuum. The residue was chromatographed over silicagel using methylene chloride/methanol/ammonia (92.5/7/0.5) as an eluent. After evaporating in vacuum 0.56 g (84.8%) of the desired product were obtained having a melting point of 212°–213° C. $^{13}$C NMR (CDCl$_3$, Ref.: TMS, additive: methanol):

| | | |
|---|---|---|
| 1 | 139.38 | S |
| 2 | 141.70 | S |
| 3 | 122.67 | S |
| 4 | 119.87 | D |
| 5 | 123.40 | D |
| 6 | 124.90 | D |
| 7 | 120.79 | S |
| 8 | 24.02 | T |
| 9 | 23.25 | T |
| 10 | 47.35 | T |
| 11 | 197.02 | S |
| 12 | 39.14 | T |
| 13 | 19.93 | T |
| 14 | 133.01 | S |
| 15 | 127.69 | |
| 16 | 129.24 | |
| 17 | 10.71 | Q |

In a similar manner was obtained: 1-(7,8-dihydro-6H-pyrazolo[4,5,1-ij]quinolin-2-yl)-2-methyl-3-(4-methyl-imidazol-5-yl)-propan-1-one; $^{13}$C NMR (CDCl$_3$, Ref : TMS)

| | | |
|---|---|---|
| 1 | 139.13 | S |
| 2 | 140.88 | S |
| 3 | 122.25 | S |
| 4 | 119.90 | D |
| 5 | 122.95 | D |
| 6 | 124.42 | D |
| 7 | 120.95 | S |
| 8 | 23.83 | T |
| 9 | 23.00 | T |
| 10 | 47.06 | T |
| 11 | 200.71 | S |
| 12 | 42.26 | D |
| 13 | 17.32 | Q |
| 14 | 28.60 | T |
| 15 | 132.88 | D |
| 16 | 128.44 | S |
| 17 | 128.31 | S |
| 18 | 10.95 | Q |

Preparation of intermediates used in the above described examples:

A.
7,8-dihydro-6H-pyrazolo[4,5,1-ij]quinoline-2-carboxylic acid (a)
1-(7,8-dihydro-6H-pyrazolo[4,5,1-ij]quinolin-2-yl)-2-phenyl-ethene.

20 g (0.5 mol) of sodium hydroxide were dissolved in 120 ml of water. A cold solution of 109 g (0.5 mol) of 8-acetyl-1-nitroso-1,2,3,4-tetrahydroquinoline and 53 g (0.5 mol) of benzaldehyde in 300 ml of ethanol was added at 0°–5° C. The mixture was stirred at 10° C. for 1 hour, 600 ml of methylene chloride were then added and the mixture was stirred for 1 hour at 10°–20° C. 500 ml of water were then added, the organic layer was separated, dried, and the solvent was distilled off. 153.5 g of crude 8-(3-phenyl-2-propen-1-on-1-yl)-1-nitroso-1,2,3,4-tetrahydroquinoline were obtained.

This crude product was dissolved in a mixture of 1000 ml of methanol and 300 ml of acetic acid. 100.9 g (1.5 mol) of zinc powder were slowly added at a temperature between −5° C. and +5° C. The mixture was then stirred for 1 hour at 0°–5° C., filtrated over hyfro, and the filtrate was evaporated in vacuum. The residue was shaken with methylene chloride and with 1N hydrochloric acid. The organic layer was separated, washed with 2N sodium hydroxide, and evaporated in vacuum. The residue was chromatographed over silicagel using methylene chloride/methanol (99.5/0.5) was an eluent. 63.2 g (49%) of the desired product were obtained after evaporating the desired fractions.

(b)
2-formyl-7,8,-dihydro-6H-pyrazolo[4,5,1-ij]quinoline 63.2 g (243 mmol) of the product obtained in (a) were dissolved in 1500 ml of ether. 1500 ml of water and 1 g of osmium tetroxide were added and the mixture was stirred for 5 minutes. 114.7 g (535 mmol) of sodium iodate were added in small portions in 45 minutes at 20° C., and stirring was continued for 2.5 hours at room temperature. Once more 1 g of osmium tetroxide was added while stirring for 5 minutes, and 52.1 g (243 mmol) of sodium iodate were added in small portions. The mixture was then washed with 1.5 l of water. The ether layer was filtrated over hyflo, dried and evaporated in vacuum. The residue was chromatographed over silicagel using methylene chloride as an eluent. 32.7 g (72.3%) of the aldehyde were obtained after evaporating the desired fractions. Melting point 119°–120° C.

(c)
7,8-dihydro-6H-pyrazolo[4,5,1-ij]quinoline-2-carboxylic acid

A solution of 51 g (0.3 mol) of silver nitrate in 75 ml of water and a solution of 37.5 g (0.67 mol) of potassium hydroxide in 675 ml of water successively were added at room temperature to a solution of 22.5 g (0.12 mol) of the product obtained in (b) in 800 ml of ethanol. The mixture was stirred for 20 hours, filtrated over hyflo and washed with water. The filtrate was shaken with methylene chloride, the water layer was separated and acidified with 250 ml of acetic acid. 20.6 g (84%) of the desired product were obtained after extracting the acid mixture with methylene chloride and evaporating the solvent. Melting point 210°–212° C. (decomposition).

In a similar manner was obtained:

6,7 8,9-tetrahydro-pyrazolo[4,5,1-jk][1]benzazepine-2-carboxylic acid; melting point 202°–204° C. (decomposition).

B. 2-acetyl-7,8-dihydro-6H-pyrazolo[4,5,1-ij]quinoline 19.7 g (0.25 mol) of pyridine were dissolved in 335 ml of methylene chloride. 15.2 (152 mmol) of chromium trioxide were added in portions under an atmosphere of nitrogen at temperatures below 35° C., and the mixture was stirred for 30 minutes. 4.0 g (0.02 mol) of 2-(1-hydroxyethyl)-7,8-dihydro-6H-pyrazolo[4,5,1-ij]quinoline (obtained by reaction of 2-formyl-7,8-dihydro-6H-pyrazolo[4,5,1-ij]quinoline with 2.5 equivalent of methylmagnesium bromide), dissolved in 40 ml of methylene chloride were then added. The mixture was stirred for a few minutes, decanted and evaporated in vacuum. The residue was chromatographed over silicagel using methylene chloride/ethyl acetate (3/1) as a eluent. 3.5 g of the desired product were obtained after evaporation of the desired fractions. Melting point 101°–102° C.

In an analogous manner was obtained: 2-propionyl-7,8-dihydro-6H-pyrazolo[4,5,1-ij]quinoline; melting point 62°–64° C.

C.
N-methyl-N{(4-methyl-1-triphenylmethyl-1H-imidazol-5-yl) methyl}amine and
N-methyl-N-{(5-methyl-1-triphenylmethyl-4-yl)methyl}amine 5 g (13.4 mmol) of the mixture of isomers of 4 (or 5)-chloromethyl-5 (or 4)-methyl-1-(triphenylmethyl)-1H-imidazole (prepared analogous to the synthesis of 4-(chloromethyl)-5-methyl-1-(triphenylmethyl)-1H-imidazole as described in European patent application 0242973) were dissolved in 30 ml of toluene. This solution was added dropwise to 50 ml of liquid methylamine and stirred for 1 hour at −6° C. After standing 60 hours at room temperature methylene chloride and 2N sodium hydroxide were added to the residue. The mixture was shaken and the organic layer was separated, washed with brine and evaporated in vacuum. The residue was chromatographed over silicagel first using methylene chloride/methanol/ammonia (89/10/1) and then methanol containing 3% by volume of triethylamine as an eluent. Two fractions were obtained: fraction 1 (1.06 g) and fraction 2 (3.56 g).

D.
{(4-methyl-1-triphenylmethyl-1H-imidazol-5-yl)methyl}amine and
{(5-methyl-1-triphenylmethyl-1H-imidazol-4-yl)methyl}amine (a) The mixture of isomers of {4(or 5)-formyl-5(or 4)-methyl-1-(triphenylmethyl)-1H-imidazole}oxim 11.6 g (170 mmol) of hydroxylamine hydrochloride were added, while stirring to a suspension of 27.9 g (79 mmol) of the mixture of isomers of 4 (or 5)-formyl-5 (or 4)-methyl-1-(triphenylmethyl)-1H-imidazole (prepared in an analogous manner to the synthesis of 4-formyl-5-methyl-1-triphenylmethyl-1H-imidazole described in EP No. 0242973) in 250 ml of absolute ethanol and 50 ml of triethylamine. The mixture was boiled for 1 hour while stirring. After cooling 200 ml of water was added dropwise. The solid was sucked off and washed with water. The filtrate was shaken with methylene chloride, the organic layer was washed with water, and evaporated. The residue obtained was combined with the solid sucked off, and the mixture was stirred with a small portion of absolute ethanol. 25.1 g of the desired product were obtained after sucking off and drying.

(b){(4(or 5)-methyl-1-triphenylmethyl-1H-imidazol-5(or 4)-yl)methyl}amine

The oxim prepared in (a) (25.1 g, 68.5 mmol) was added in portions, while stirring at 20° C., to a suspension of 13 g (340 mmol) of lithiumaluminium hydride in 250 ml of tetrahydrofuran. When addition was completed the mixture first was stirred for 30 minutes at 20° C. and then boiled for 1 hour while stirring 13 ml of water, 26 ml of 2N sodium hydroxide and 13 ml of water successively were added dropwise after cooling, keeping the temperature below 25° C. The mixture was then boiled for 10 minutes and cooled. The solid was filtered off and washed with tetrahydrofuran. The filtrate was evaporated and the residue was chromatographed over silicagel first using methylene chloride/methanol (90/10) and then methanol containing 3% by volume of triethylamine as an eluent. 11.9 g of the product were obtained after evaporating the desired fractions. Melting point 169°–176° C.

We claim:

1. Compounds of formula (1)

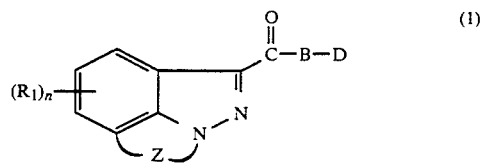

wherein

Z, together with the carbon and the nitrogen and the intermediate carbon, forms a heterocyclic group consisting of 6 ring atoms;

B is oxygen or —CH($R_4$)— or —N$R_4$—, wherein $R_4$ is hydrogen, straight or branched alkyl having 1-6 carbon atoms, or benzyl;

D is a group B—C—D of the formulae 2-9:

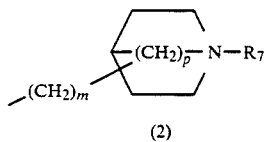

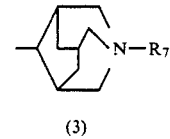

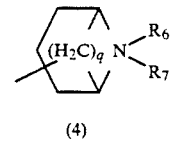

-continued

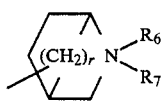

(5)

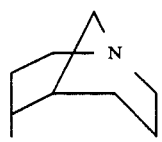

(6)

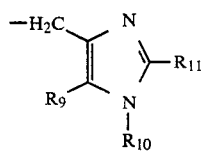

(7)

-continued

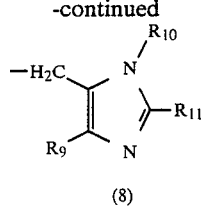

(8)

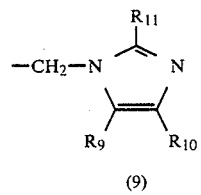

(9)

wherein p is 1 or 2; m is 0 or 1; q is 2, 3 or 4; r is 1, 2 or 3; $R_6$ is hydrogen or alkyl of 1–6 carbon atoms; one of $R_9$, $R_{10}$ and $R_{11}$ is hydrogen, alkyl of 1–4 carbon atoms, cycloalkyl of 3–6 carbon atoms or alkenyl of 2–4 carbon atoms and the other two groups are independently of each other hydrogen or alkyl of 1–4 carbon atoms;

and the pharmaceutically acceptable acid addition salts thereof.

2. Pharmaceutical compositions which comprise at least one compound as claimed in claim 1 as an active substance and a pharmaceutically acceptable carrier.

3. A method of preparing pharmaceutical compositions as claimed in claim 2, characterized in that the active compound is brought into a form suitable for administration.

* * * * *

UNITED STATES PATENT AND TRADEMARK OFFICE
CERTIFICATE OF CORRECTION

PATENT NO. : 4,950,759
DATED : AUGUST 21, 1990
INVENTOR(S) : Ineke van WIJNGAARDEN ET AL It is certified that error appears in the above-identified patent and that said Letters Patent is hereby corrected as shown below:

Column 20, line 39 (Claim 1), after "wherein" insert

-- $(R_1)_n$ is hydrogen; --

Column 22, line 19, before "one of" insert --$R_7$ is absent or is an oxygen atom;--.

Signed and Sealed this

First Day of February, 1994

Attest:

BRUCE LEHMAN

*Attesting Officer*     *Commissioner of Patents and Trademarks*